United States Patent [19]

Buckland

[11] Patent Number: 5,488,162
[45] Date of Patent: Jan. 30, 1996

[54] PROCESS FOR PREPARING O-ALKYLHYDROXYLAMINE SALTS WITHOUT THE ISOLATION OF INTERMEDIATES

[76] Inventor: Paul R. Buckland, 1 Lawton Dr., Rochester, N.Y. 14534

[21] Appl. No.: 176,985

[22] Filed: Jan. 3, 1994

[51] Int. Cl.$^6$ .................................. C07C 209/00
[52] U.S. Cl. .................. 564/301; 564/256; 564/259
[58] Field of Search ........................ 564/256, 259, 564/301

[56] References Cited

U.S. PATENT DOCUMENTS

| | | | |
|---|---|---|---|
| 4,507,248 | 3/1985 | Mathew et al. | 260/500.5 H |
| 5,075,504 | 12/1991 | Schneider | 564/301 |
| 5,393,921 | 2/1995 | Lazar | 562/512 |

FOREIGN PATENT DOCUMENTS

| | | |
|---|---|---|
| 0158159 | 10/1985 | European Pat. Off. . |
| 3258757 | 11/1991 | Japan . |
| WO89/11473 | 11/1989 | WIPO . |

OTHER PUBLICATIONS

Derwent Abstract WPI Acc. No. 92–004477/01 (JP 3258757) (1992).
Derwent Abstract WPI Acc. No. 84–309712/50 (JP 8368791) (1984).
Derwent Abstract WPI Acc. No. 88–072313/11 (DE 3631071) (1988).

*Primary Examiner*—Peter O'Sullivan
*Attorney, Agent, or Firm*—John D. Thallemer; Harry J. Gwinnell

[57] ABSTRACT

This invention relates to a process for preparing aqueous solutions of O-alkylhydroxylamine salts. The process involves converting hydroxylamine salts to their O-alkyl derivatives without the isolation of intermediates. More specifically, the process involves three steps. The first step, Step (A), involves forming a ketoxime. The second step, Step (B), involves adding an alkylating agent to the ketoxime formed in Step (A). The third step, Step (C), involves hydrolysing the alkylated ketoxime formed in Step (B) to yield an O-alkylhydroxylamine salt. O-alkylhydroxylamine salts are important intermediates in the preparation of herbicides.

2 Claims, No Drawings

PROCESS FOR PREPARING O-ALKYLHYDROXYLAMINE SALTS WITHOUT THE ISOLATION OF INTERMEDIATES

FIELD OF INVENTION

This invention relates to a process for preparing aqueous solutions of O-alkylhydroxylamine salts. The process involves converting hydroxylamine salts to their O-alkyl derivatives without the isolation of intermediates. More specifically, the process involves three steps. The first step, Step (A), involves forming a ketoxime. The second step, Step (B), involves adding an alkylating agent to the ketoxime formed in Step (A). The third step, Step (C), involves hydrolysing the alkylated ketoxime formed in Step (B) to yield an O-alkylhydroxylamine salt. O-alkylhydroxylamine salts are important intermediates in the preparation of herbicides.

BACKGROUND OF THE INVENTION

O-alkylhydroxylamines have been prepared by reacting oximes with alkyl halides under basic conditions to give O-alkyl oximes, followed by acid catalyzed hydrolysis of the O-alkyl oxime. For example, PCT Application WO 8911473 discloses a process for producing O-substituted oxime compounds in which a large excess of propanone oxime in toluene is reacted with an aqueous alkali metal hydroxide to give, after azeotropic distillation, the oxime salt which on reaction with an alkyl halide followed by further distillation, acidification and extraction with toluene affords the O-alkyl oxime in moderate purity (83.5%). European Pat. No. 85-103052 discloses a similar process for the synthesis of O-alkyl oximes which were subsequently hydrolysed using aqueous hydrochloric acid to give the O-alkylhydroxylamines.

Jap. Pat. No. 03258757 discloses a process in which acetone oxime is reacted with sodium hydride and N,N-dimethylformamide at 60° to 70° C. and the resulting oxime salt subsequently reacted with an alkyl bromide to give a low yield (37%) of an O-alkyl acetone oxime. Jap. Pat. No. 83-68791 discloses a similar process in which the acetone oxime salt is generated below 10° C. and subsequently reacted with a solution of an alkyl halide in dimethoxyethane to give a low yield (52.4%) of an O-alkyl oxime.

German Pat. No. 86-3631071 discloses a procedure for the preparation of O-substituted hydroxylamine hydrochlorides in which a O-alkyl acetone oxime, present in a mixture of 1,4-dioxane, water and hydrochloric acid, is hydrolysed and the acetone continuously removed by distillation through a bubble tray column.

The above methods suffer from one or more disadvantages such as isolation of intermediates which is inconvenient and costly, low yields and use of undesirable solvents. In contrast, the present invention uses a process which does not require isolation of intermediates, produces high yields of the O-alkyl oximes and their O-alkylhydroxylamine derivatives, and requires only one organic solvent which can be recovered and reused.

The process of the present invention for preparing O-alkylhydroxylamines is represented as follows:

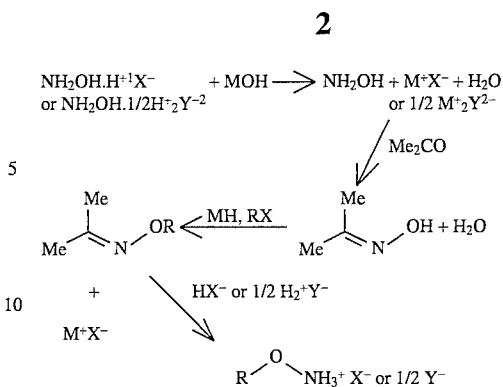

SUMMARY OF THE INVENTION

Accordingly, it is one object of the present invention to provide a process for preparing O-alkylhydroxylamines.

Accordingly, it is another object of the invention to provide a process for preparing O-alkylhydroxylamines without isolation of intermediates.

Accordingly, it is a further object of the invention to provide a process for preparing the O-alkylhydroxylamines in high yield and high purity.

These and other objects are accomplished herein by a process for preparing O-alkylhydroxylamines without isolation of intermediates, said process comprising forming a ketoxime; adding an alkylating agent to the ketoxime; and hydrolysing the alkylated ketoxime formed in Step (B) to yield an O-alkylhydroxylamine salt.

DESCRIPTION OF THE INVENTION

The process of the present invention for preparing O-alkylhydroxylamines without isolation of intermediates involves three steps. The first step, Step (A), involves forming a ketoxime. A hydroxylamine salt such as hydroxylamine hydrochloride or hydroxylamine sulfate in water is neutralized by addition of an equivalent amount of alkali metal hydroxide or ammonium hydroxide. Any alkali metal hydroxide or ammonium hydroxide compound can be employed such as lithium hydroxide, potassium hydroxide, calcium hydroxide, magnesium hydroxide, and sodium hydroxide. Alkali metal hydroxide compounds are preferred for use in the practice of this invention. Particularly preferred for use are potassium hydroxide and sodium hydroxide, and most preferred is sodium hydroxide. The reaction temperature should be maintained at 15° C. to 55° C. Preferably, the reaction temperature is maintained at 20° C. to 50° C., more preferably, 25° C. to 35° C. Cooling may be necessary to control the reaction temperature. The pH of the hydroxylamine solution should be 11 to 13.

The aqueous solution of hydroxylamine is reacted with an equivalent amount or slight excess (up to 10%) of an aliphatic ketone having 3 to 10 carbon atoms at a temperature of 20° C. to 100° C. to produce a ketoxime. A preferred temperature range is 30° C. to 60° C. Cooling may be necessary to control the reaction temperature. Examples of ketones which are useful in the present invention are acetone, diethyl ketone, and 2-butanone. Preferably, the aliphatic ketone is acetone. The final pH of the mixture, which if necessary can be adjusted by addition of an acid, such as hydrochloric acid, should be 4 to 7 to ensure that any unreacted hydroxylamine remains in the aqueous phase as a salt. A two phase system results which contains an upper layer of ketoxime and a lower aqueous layer of inorganic salt solution. The lower aqueous layer containing an alkali metal or amine salt is separated.

The second step, Step (B), involves adding an equivalent amount of an alkylating agent to the ketoxime formed in Step (A). Suitable alkylating agents include an alkyl halide RX, alkyl sulfonate $ROSO_2Z$ or alkyl sulfate $R_2SO_4$, wherein R is primary $C_1$ to $C_{15}$ substituted or unsubstituted linear, branched, unsaturated or saturated alkyl or any combination thereof. The alkyl halide RX may be a chloride, bromide or iodide wherein X=Cl, Br or I. Examples of alkyl halides are allyl chloride, benzyl bromide, iodomethane, benzyloxybenzyl chloride, 1-bromo-2-methylpropane, E-1,3-dichloropropene, Z-1,3-dichloropropene, 8-bromooctene, 1-bromobutane and propargyl chloride.

The alkyl sulfonate may be an alkyl arylsulfonate wherein Z is substituted or unsubstituted aryl, or an alkyl alkanesulfonate wherein Z is substituted or unsubstituted alkyl. Examples of alkyl sulfonates are heptyl methanesulfonate, 2-methylbutyl methanesulfonate, 2,2,2-trifluoroethyl p-toluenesulfonate, 0-benzyl p-toluenesulfonate and propargyl benzenesulfonate. Examples of alkyl sulfates are dimethyl sulfate and ethyl sulfate.

The alkylating agent may act as a solvent for the ketoxime in the case where the alkylating agent is sufficiently stable to aqueous conditions (pH 4 to 7). Thus, in such a case the alkylating agent may be added to the ketoxime before separation of the lower aqueous layer containing an alkali metal or amine salt. (See Example 1 supra.)

The mixture of alkylating agent and ketoxime is added to a stirred suspension of an alkali metal hydride MH, wherein M is lithium, sodium, or potassium in a water miscible amide solvent at $-10°$ to $10°$ C., to form an O-alkylketoxime. Conducting the reaction below 10° C. is preferable to minimize formation of by-products as deduced from a comparison of the NMR spectra of the product obtained at various reaction temperatures.

The alkali metal hydride is preferably sodium hydride or an oil dispersion of this material. Suitable examples of water miscible amide solvents are N,N-dimethylformamide, N,N-diethylformamide, N,N-dimethylacetamide, N,N-diethylacetamide, N,N-dimethylpropanamide, N,N-diethylpropanamide and formamide. The water miscible amide solvent may also include a combination of such solvents. The use of amide solvents allows rapid and complete alkylation. Other solvents such as toluene were found to be unsuitable because incomplete alkylation was achieved. Use of nucleophilic bases e.g. sodium methoxide in methanol led to incomplete formation of ketoxime salt even when the majority of solvent was removed because of the equilibrium nature of the reaction. This, together with reaction of residual base with the alkylating agent, resulted in lower yields of O-alkylketoxime, compared with those obtained in the present invention.

Water and an alkane solvent are added to the reaction mixture containing the O-alkylketoxime, to give a two phase mixture comprising an upper alkane solvent layer containing the O-alkylketoxime together with mineral oil (present when an oil dispersion of an alkali metal hydride is used), unreacted alkylating agent and traces of by-products formed during alkylation, and a lower aqueous layer containing the amide solvent. Suitable alkane solvents are hexane, heptanes and octanes. The lower aqueous layer containing an alkali metal or amine salt and water miscible amide solvent is removed by methods known in the art.

The third step, Step (C), involves hydrolysing the alkylated ketoxime formed in Step (B). A concentrated mineral acid is added to the alkane solution containing the O-alkylketoxime in an alkane solvent as formed in Step (B), to give a two phase mixture comprising a lower layer of the O-alkylketoxime in mineral acid and an upper layer of the alkane solvent solution containing mineral oil (present when an oil dispersion of an alkali metal hydride is used), unreacted alkylating agent and traces of by-products formed during alkylation. Use of an alkane solvent is effective in removing these impurities. A suitable example of a concentrated mineral acid is 37% hydrochloric acid. An antioxidant such as hydroquinone may be added at this stage to prevent discoloration of the final product.

The alkane solution is removed either by siphonation or by allowing the acid layer to drain from the bottom of the vessel into a second vessel. The mineral acid solution of O-alkylketoxime is heated and the ketone formed is removed by distillation, to give an aqueous solution of O-alkylhydroxylamine. The application of reduced pressure is preferred because it aids in the removal of the ketone and allows the distillation to be conducted at a lower temperature, which is important because carbonization can occur at elevated temperatures. Preferably, the distillation is conducted at a temperature below 60° C. The O-alkylhydroxylamine salts are important intermediates in the preparation of herbicides.

The process of this invention is carried out over a period of time sufficient to produce the desired compound in adequate yield. Reaction times are influenced to a significant degree by the reactants; the reaction temperature; the concentration and choice of reactants; the choice and concentration of reaction solvent and by other factors known to those skilled in the art.

The process of the present invention will be further illustrated by a consideration of the following examples, which are intended to be exemplary of the invention. All parts and percentages are on a weight basis unless otherwise stated.

EXAMPLE 1

Preparation of Acetone Oxime

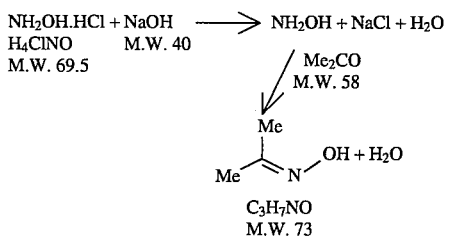

Hydroxylamine hydrochloride (153.6 grams, 2,213 mole) and water (309 grams) were added to a 2000 ml four necked flask, Flask I, equipped with an overhead stirrer, double surface condenser, thermometer and addition funnel. The mixture was stirred for 15 minutes during which the temperature fell to 6° C. and most of the solid dissolved. 50% sodium hydroxide (182 grams, 2.27 mole) was added with cooling, keeping the temperature at 25° C. to 35° C. The resulting clear solution had a pH 12. Acetone (135 grams, 2.41 mole, 10% excess) was added with rapid stirring over 20 minutes allowing the temperature to rise to 60° C. The mixture (pH 9) was stirred for a further 40 minutes during which it was carefully adjusted to pH 6 by addition of 11.6M-hydrochloric acid (2.4 grams). 1,3-dichloropropene (222 grams, 2 mole) was added to the warm (40° C.) mixture and the layers allowed to separate over 2 hours. The bottom aqueous sodium chloride layer (590 grams), containing a small amount of insoluble material, was run off and discarded. The top layer (a yellow oil) 368.7 grams (Note 1) was used directly in the next step of alkylation.

Note 1. The NMR spectrum was consistent with an approximate equimolar mixture of dichloropropene. The spectrum displayed 4 mole percent acetone but no water. The weight of the mixture indicated that 146 grams of acetone oxime (90% yield) was present.

EXAMPLE 2

Preparation of O-(3-chlor-2-E-propenyl)-2-propanone oxime

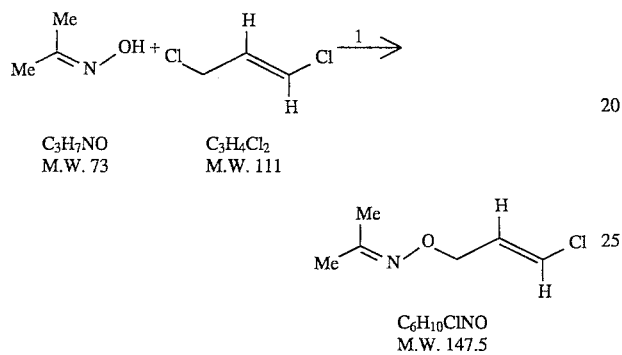

60% Sodium hydride (100 grams, 2.5 mole) and N,N-dimethylformamide (300 ml, 283 grams) were placed in a four necked 3000 ml flask equipped with an overhead stirrer, thermometer and nitrogen inlet. The mixture was cooled to 0° C. before a mixture of acetone oxime (146.7 grams, 2 mole) and E-1,3-dichloropropene (222 grams, 2 mole) which was prepared in Example 1, was added dropwise over 2 hours maintaining the temperature at 4° C. to 8° C. with the aid of an ice/acetone bath. Hydrogen was evolved but no thickening and very little foaming occurred.

The mixture was stirred for an additional two hours at 4° C. to 6° C. (Note 1). Heptanes (200 ml, 137 grams) were added (Note 2). Cold (5° C.) water (1200 grams) was added dropwise at first and then more rapidly. The temperature rose to 25° C. After stirring for 5 minutes the layers which contained a little dark red insoluble material were allowed to separate. The bottom aqueous layer (1634 grams, 1550 ml) containing most of the insolubles was run off and discarded. The heptanes solution was washed with water (200 ml) and the layers allowed to separate. The bottom aqueous layer (203.8 grams) was run off and discarded.

The water wash was repeated, discarding 200 grams aqueous (pH 9). The top pale orange heptanes layer weighed 405 grams (contains c.a. 405−40−137=228 grams of product). Hydroquinone (100 mg) (Note 3) was added followed by cold (5° C.) 11.6M hydrochloric acid (1310 grams, 1091 ml). The mixture was stirred for 5 minutes. The layers were allowed to separate and the bottom layer consisting of a hydrochloric acid solution of product (1518 grams) was removed (Note 4) to the 2000 ml flask (A) ready for distillation. The top heptanes layer (190.9 grams) (Note 5) was discarded.

Note 1. The mixture was periodically analysed by NMR spectroscopy. 0.5 ml was removed and 2 mls water was added. The NMR spectrum (d6 DMSO) of the top layer indicated that conversion of dichloropropene ($CH_2$; 4.2 ppm) to product ($CH_2$; 4.5 ppm) was approximately 82% (2 hr) and 96% (4 hr). The NMR spectrum contained fewer extraneous peaks than the spectrum of a sample obtained from a similar experiment run at room temperature.

Note 2. The use of heptanes facilitates layer separation and is effective in the subsequent removal of mineral oil contaminant and other impurities e.g. unreacted dichloropropene.

Note 3. Hydroquinone was added to help prevent oxidation and discoloration of the eventual hydroxylamine product.

Note 4. An NMR spectrum (d6 DMSO) of the combined hydrochloric acid extracts was consistent with the desired product together with some of the desired hydroxylamine derivative and acetone. No mineral oil (from sodium hydride), dichloropropene, N,N-dimethylformamide or other impurities were present. The weight of the hydrochloric acid solution implies that 208 grams (71% overall) of product was present.

Note 5. An NMR spectrum confirmed that the top layer consisted of heptanes, mineral oil, dichloropropene and an unidentified product ($CH_2$; 5.2 ppm). The low field nature of this signal suggested that the unidentified by-product (<2%) may be the nitrone derived from N-alkylation of the oxime. No product was present in the heptanes layer.

EXAMPLE 3

Preparation of E—O-(3-chloro-2-propenyl)hydroxylamine hydrochloride

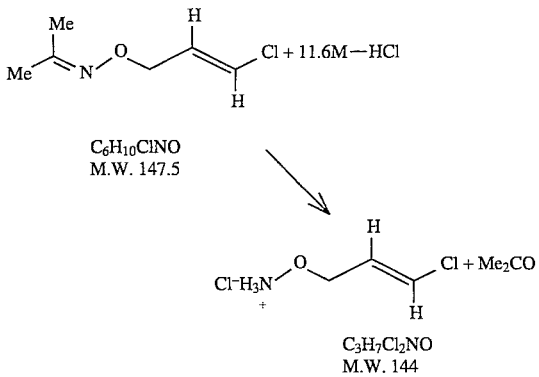

The O-(3-chloro-2-E-propenyl)-2-propanone oxime solution prepared in Example 2 (1518 grams) containing approximately 208 grams of 0-(3-chloro-2-E-propenyl)-2-propanone oxime and 11.6M-hydrochloric acid was heated (oil bath set at 100° C.) under reduced pressure (50 mm) (Note 1) until crystallization had begun at which point 510 ml distillate (571 grams) b.p. 53 to 55° C. had collected over 6 hours (Note 2). More 1.6M-hydrochloric acid (1200 grams, 1000 ml) was added and the distillation repeated over 4 hours. Finally a mixture of 11.6-M hydrochloric acid (300 grams, 250 ml) and water (500 grams) was added and the volume reduced to 500 ml over 2 hours. Charcoal (5 grams) was added and after heating at 50° C. the mixture was filtered to give an approximately 40% solution of the hydroxylamine hydrochloride product (514 grams) (Note 3). Thus, the yield of O-alkylhydroxylamine salt was 205.6 grams (71% overall yield based on E-1,3-dichloropropene.

Note 1. A previous attempt in which the distillation was carried out at atmospheric pressure (oil bath 130° C.) led to considerable decomposition as evidenced from NMR analysis and appearance of the solution (dark brown+ carbonized material present).

Note 2. The progress of the reaction was determined using NMR (d6 DMSO) analysis. This showed that the percent conversion of the oxime ether to product after 6 hours was 79%.

Note 3. NMR indicated that a 99% conversion to product had occurred.

Many variations will suggest themselves to those skilled in this art in light of the above detailed description. All such obvious modifications are within the full intended scope of the appended claims.

What is claimed is:

1. A process for preparing O-alkylhydroxylamines without isolation of intermediates, said process comprising the following steps:

(I) neutralizing an aqueous solution of a hydroxylamine salt to produce hydroxylamine;

(II) reacting an aliphatic ketone having 3 to 10 carbon atoms with hydroxylamine formed in Step (I) to produce a two phase system comprising an upper layer of ketoxime and a lower layer of inorganic salt solution;

(III) removing the inorganic salt solution;

(IV) adding an alkylating agent to the ketoxime formed in Step (II) to form a alkylating agent/ketoxime mixture;

(V) adding the alkylating agent/ketoxime mixture to a suspension of an alkali metal hydride in a water miscible amide solvent to form an O-alkylketoxime;

(VI) adding water and an alkane solvent to the O-alkylketoxime formed in Step (V) to give a two phase mixture comprising an upper layer of the O-alkylketoxime in the alkane solvent and a lower aqueous layer containing the amide solvent;

(VII) removing the aqueous solution;

(VIII) adding a concentrated mineral acid to the alkane solution formed in Step (VI) to give a two phase mixture comprising a lower layer of the O-alkylketoxime in mineral acid and an upper layer of the alkane solvent solution;

(IX) removing the alkane solution;

(X) heating the mineral acid solution of O-alkylketoxime formed in Step (VIII) and removing by distillation the ketone formed, to give an aqueous solution of O-alkylhydroxylamine.

2. A process for preparing O-alkylhydroxylamines without isolation of intermediates, said process comprising the following steps:

(I) neutralizing an aqueous solution of a hydroxylamine salt to produce hydroxylamine;

(II) reacting an aliphatic ketone having 3 to 10 carbon atoms with hydroxylamine formed in Step (I) to produce a two phase system comprising an upper layer of ketoxime and a lower layer of inorganic salt solution;

(III) adding an alkylating agent to the ketoxime formed in Step (II) to form a alkylating agent/ketoxime mixture;

(IV) removing the inorganic salt solution;

(V) adding the alkylating agent/ketoxime mixture to a suspension of an alkali metal hydride in a water miscible amide solvent to form an O-alkylketoxime;

(VI) adding water and an alkane solvent to the O-alkylketoxime formed in Step (V) to give a two phase mixture comprising an upper layer of the O-alkylketoxime in the alkane solvent and a lower aqueous layer containing the amide solvent;

(VII) removing the aqueous solution;

(VIII) adding a concentrated mineral acid to the alkane solution formed in Step (VI) to give a two phase mixture comprising a lower layer of the O-alkylketoxime in mineral acid and an upper layer of the alkane solvent solution;

(IX) removing the alkane solution;

(X) heating the mineral acid solution of O-alkylketoxime formed in Step (VIII) and removing by distillation the ketone formed, to give an aqueous solution of O-alkylhydroxylamine.

* * * * *